United States Patent [19]

Misaki et al.

[11] 4,246,342
[45] Jan. 20, 1981

[54] PROCESS FOR THE MANUFACTURE OF PYRUVATE OXIDASE, AND ANALYTICAL METHOD AND KIT FOR THE USE OF THE SAME

[75] Inventors: Hideo Misaki; Kazuo Matsuura; Saburo Harada; Satoshi Takenaka; Yoshifumi Horiuchi, all of Shizuoka, Japan

[73] Assignee: Toyo Jozo Kabushiki Kaisha, Shizuoka, Japan

[21] Appl. No.: 22,442

[22] Filed: Mar. 21, 1979

[30] Foreign Application Priority Data

Mar. 25, 1978 [JP] Japan ............................... 53/34687
Jul. 14, 1978 [JP] Japan ............................... 53/86350

[51] Int. Cl.$^3$ .......................... C12Q 1/26; C12N 9/08
[52] U.S. Cl. ........................................ 435/25; 435/16; 435/17; 435/19; 435/192; 435/810; 435/822; 435/885

[58] Field of Search ................... 435/189, 192, 25, 17, 435/19, 16

[56] References Cited
PUBLICATIONS

Dixon et al., Enzymes, 2nd Edition, 1964, pp. 684–685.
Colowick et al., editors, Methods in Enzymology, vol. 1, pp. 482–490 (1955).

Primary Examiner—Lionel M. Shapiro
Attorney, Agent, or Firm—Young & Thompson

[57] ABSTRACT

Pyruvate oxidase can be produced by culturing Pediococcus sp. B-0667, Streptococcus sp. B-0668, *Aerococcus viridans* IFO-12219 or *Aerococcus viridans* IFO-12317. It is useful for analysis for pyruvic acid, because it catalyzes the reaction of pyruvic acid, phosphate and oxygen to form acetylphosphate, carbon dioxide and hydrogen peroxide. A kit containing the various reagents for such analysis is also provided by this invention.

10 Claims, 12 Drawing Figures

○—○ : Pediococcus SP. B-0667
△—△ : Streptococcus SP. B-0668
□—□ : Aerococcus Viridans IFO 12219
☆—☆ : Aerococcus Viridans IFO 12317

○—○ : Pediococcus SP. B-0667
△—△ : Streptococcus SP. B-0668
□—□ : Aerococcus Viridans IFO 12219
☆—☆ : Aerococcus Viridans IFO 12317

○—○ : Pediococcus SP. B-0667 (Phosphate Buffer)
●—● :      〃                〃       (Tris-HCℓ Buffer)
□—□ : Streptococcus SP. B-0668 (Phosphate Buffer)
■—■ :      〃                〃       (Tris-HCℓ Buffer)
△—△ : Aerococcus Viridans IFO 12219 (Phosphate Buffer)
▲—▲ :      〃          〃       〃    (Tris-HCℓ Buffer)
☆—☆ : Aerococcus Viridans IFO 12317 (Phosphate Buffer)
★—★ :      〃          〃       〃    (Tris-HCℓ Buffer)

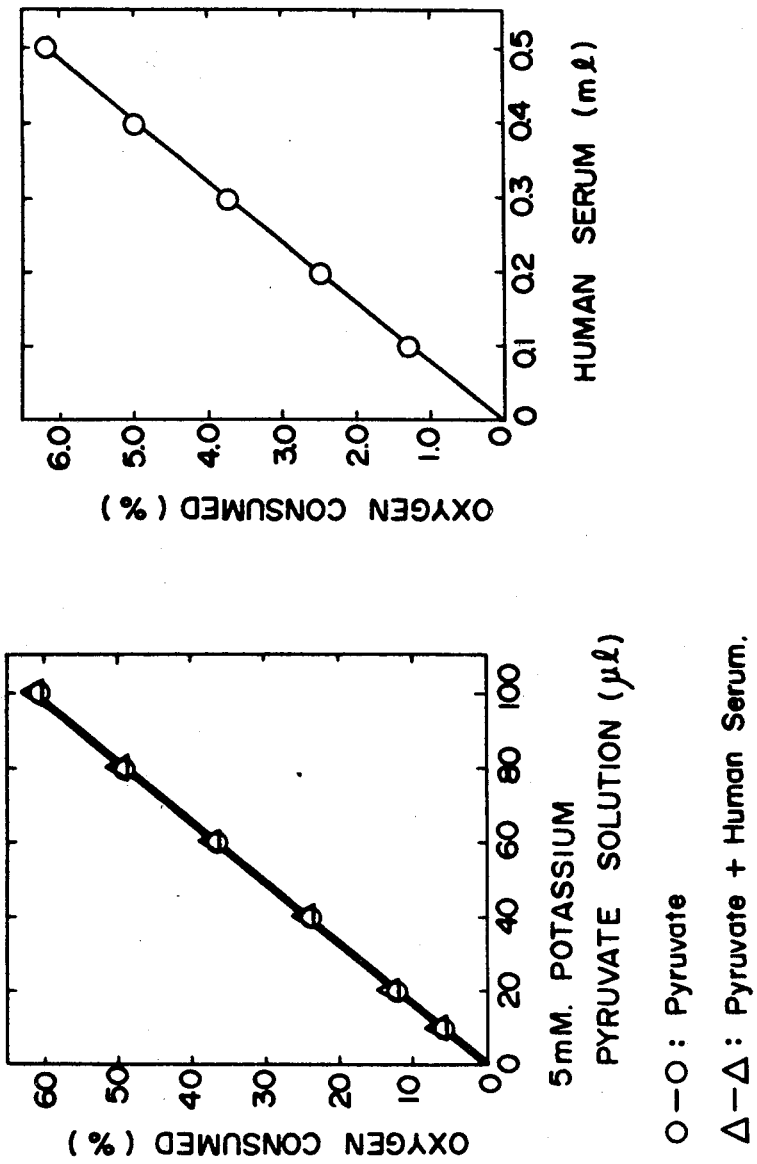

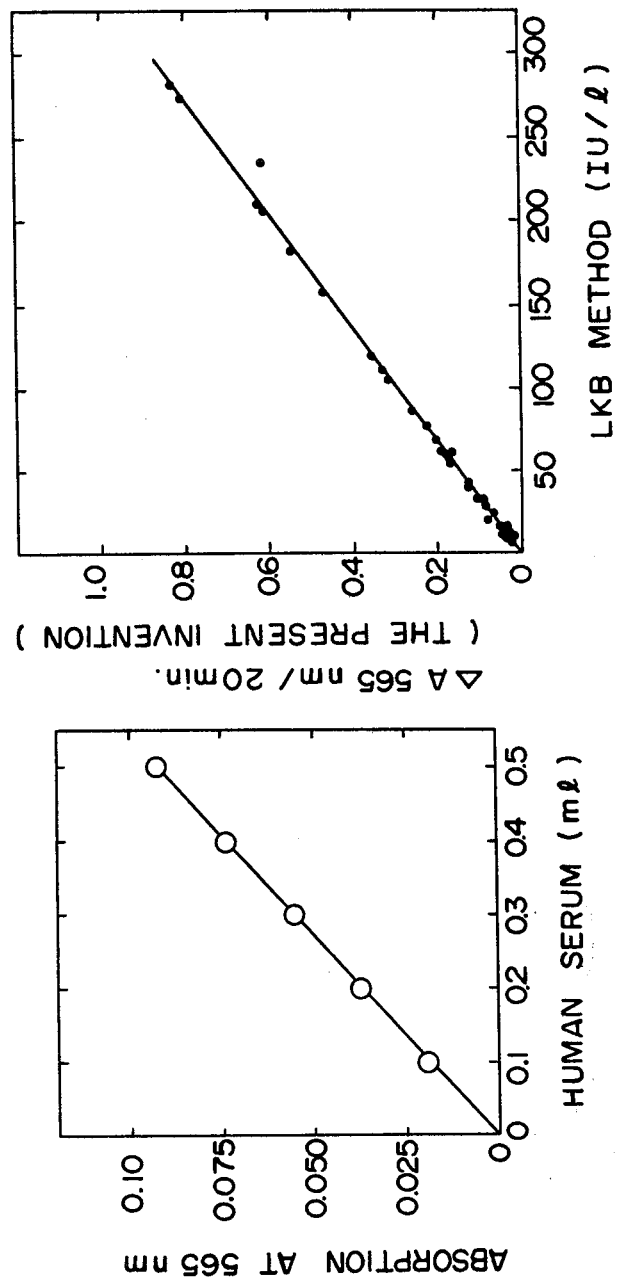

O—O : +ADP
△—△ : +H₂O₂

PROCESS FOR THE MANUFACTURE OF PYRUVATE OXIDASE, AND ANALYTICAL METHOD AND KIT FOR THE USE OF THE SAME

This invention relates to a process for the manufacture of pyruvate oxidase and its use in quantitative analysis and a kit for such analysis.

Pyruvate oxidase is a hitherto-known enzyme which catalyzes a reaction of pyruvic acid, phosphate and oxygen to form acetylphosphate, carbon dioxide and hydrogen peroxide and has heretofore been derived from a strain of *Lactobacillus derbruckii*.

It has now been found that an enzyme pyruvate oxidase can be produced by culturing bacterial strains B-0667 belonging to genus Pediococcus and B-0668 belonging to genus Streptococcus isolated from a soil sample collected in a radish field in Ohito-cho, Tagata-gun, Shizuoka-ken, Japan, and that the pyruvate oxidase produced therefrom can be used for pyruvic acid analysis in a sample containing pyruvic acid or various systems which liberate pyruvic acid. We have also found that this enzyme can be used for the quantitative analysis of pyruvic acid, the measurement of the enzyme activity of enzyme reaction systems which form pyruvates, and the quantitative determination of the enzymes and the substrates thereof. Pyruvic acid can be analyzed by reacting a sample containing pyruvic acid with a reaction system comprising at least pyruvate oxidase, flavin adenine dinucleotide (hereinafter called as FAD), thiamine pyrophosphate, oxygen and phosphate, and there has been discovered an excellent kit for pyruvate analysis and analytical methods for pyruvic acid.

Further, it has now been found that adding a salt which liberates calcium ions, cobalt ions, magnesium ions or manganese ions to the said reaction system results in an improvement of the analysis. Addition of chromogen or fluorescent indicators to the reaction system provides a convenient and excellent analytical tool. Also there has been discovered a process for the manufacture of an enzyme pyruvate oxidase.

An object of the present invention is accordingly to provide a kit for quantitative analysis, especially a reaction system containing pyruvate oxidase.

Another object of the present invention is to provide an analytical method for determining pyruvic acid in a sample containing pyruvic acid or a pyruvic acid liberating system, which method comprises treating a sample with a reaction system containing pyruvate oxidase and measuring the consumed component or generated component.

A further object of the present invention is to provide a process for the manufacture of pyruvate oxidase which comprises culturing a pyruvate oxidase-producing microorganism belonging to genus Pediococcus, Streptococcus or Aerococcus in a nutrient culture medium and isolating the pyruvate oxidase thus produced from the cultured medium.

Other objects, features and advantages of the present invention will become apparent from a consideration of the following description, taken in connection with the accompanying drawings, which are graphs illustrating the present invention, and in which more particularly:

FIG. 4 shows the results of analysis of pyruvic acid by oxygen electrode using pyruvate oxidase.

FIG. 5 shows the results of analysis of serum by oxygen electrode using pyruvate oxidase.

FIG. 7 shows the results of quantitative analysis of serum pyruvic acid using pyruvate oxidase.

FIG. 11 is a correlation diagram of analysis of GPT-activity using pyruvate oxidase.

Figure 1:
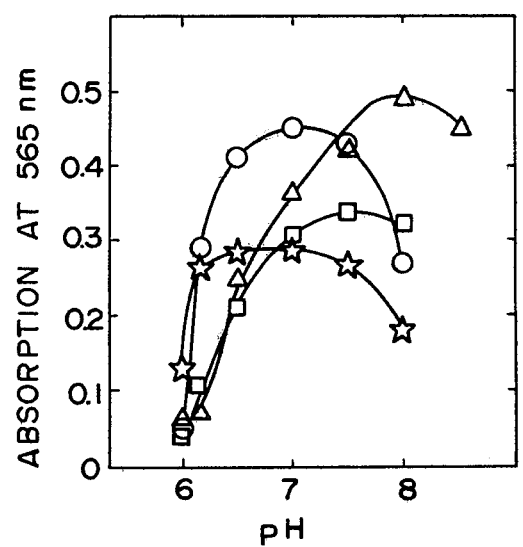
FIG. 1 is a family of curves of optimum pH of pyruvate oxidase.

An enzyme pyruvate oxidase in this invention catalyzes an oxidative reaction of pyruvic acid, inorganic phosphate and oxygen to form acetylphosphate, carbon dioxide and hydrogen peroxide, and is preferably manufactured by culturing a pyruvate oxidase-producing microbial strain belonging to genus Pediococcus, Streptococcus or Aerococcus, for example Pediococcus sp. B-0667, Streptococcus sp. B-0668, *Aerococcus viridans* IFO 12219 or IFO 12317.

The isolated strains B-0667 and B-0668 hereinabove have the following taxonomical properties:

A. Observations on various media, cultured at 30° C. for 2 days:

| | Strain B-0667 | strain B-0668 |
|---|---|---|
| Tryptosoybroth: | weak growth, homogeneously turbid, later wooly precipitation. | weak growth, homogeneously turbid, later wooly precipitation. |
| Tryptosoy agar slant: | weak growth, pale yellowish gray, no lustre. no production of soluble pigment. | weak growth, pale yellowish gray, no lustre. no production of soluble pigment. |
| Tryptosoy agar plate: | colony; small and flat. | colony; small and flat. |
| Gelatin slab: | growth along stabbed line. no gelatin liquefaction. | growth along stabbed line. no gelatin liquefaction. |
| BCP milk (14 days): | no change. | no change. |

B. Microscopic observation:

| | Strain B-0667 | Strain B-0668 |
|---|---|---|
| Shape: | Spherical, ovoid, pairs, tetra-shaped or short chain. | Spherical, ovoid, pairs, tetra-shaped or short chain. |
| Size: | 0.5–1.0 × 0.5–1.0 μ | 0.8–1.0 × 1.0–1.2 μ |
| Motility: | − | − |
| Spore: | − | − |
| Gram's stain: | + | + |
| Acid-fast strain: | − | − |

| C. Physiological properties: | Strain B-0667 | Strain B-0668 |
|---|---|---|
| Growth temperature: 45° C. | − | − |
| 37° C. | + | + |
| 30° C. | + | + |
| 26° C. | + | + |
| 10° C. | + | + |
| 5° C. | ± or (+) | ± or (+) |
| Halotolerance: NaCL 10% | + | − |
| 6.5% | + | + |
| 5.0% | + | + |
| 1.0% | + | + |
| 0% | + | − |
| OF-test: | fermentative | fermentative |
| Behavior in oxygen: | facultative anaerobic | facultative anaerobic |
| Nitrate reduction: | − | − |
| Indole formation: | − | − |
| Hydrogen sulfate formation: | − | − |
| Gelatin hydrolysis: | − | − |
| Starch hydrolysis: | − | − |
| Esculin hydrolysis: | + | + |
| Acetoin formation: | − | − |
| MR-test | − | − |
| Catalase: | − | − |
| Oxidase: | − | − |
| Urease (SSR): | − | − |
| Urease (Christensen): | − | − |
| Utilization of citric acid (Christensen): | − | − |
| Acid formation from sugar: | | |
| adonitol: | − | − |
| L(+)-arabinose: | − | − |
| cellobiose: | + | + |
| dulcitol: | − | − |
| meso-erythritol: | − | − |
| fructose: | + | + |
| fucose: | − | − |
| galactose: | + | + |
| glucose: | + | + |
| glycerol: | − | − |
| inositol: | − | − |
| inulin: | − | − |
| lactose: | + | + |
| maltose: | + | + |
| mannitol: | + | − |
| mannose: | + | + |
| melezitose: | − | − |
| melibiose: | + | − |
| raffinose: | + | − |
| L(+)-rhamnose: | − | − |
| salicin: | (+) | − |
| L-sorbose: | − | − |
| sorbitol: | − | − |
| starch: | − | − |
| sucrose: | + | + |
| trehalose: | + | + |
| xylose: | − | − |
| Tolerance at 60° C. for 30 min. | − | + |

Consulting "Bergey's Manual of Determinative Bacteriology", 8th Ed., 1974 and S. T. Cowan and K. J. Steel, "Manual for the Identification of Medical Bacteria", Cambridge Press, 1974, the strain B-0667 and B-0668 having the taxonomical properties hereinabove, especially Gram positive cocci, catalase and oxidase negative, fermentative acid formation from glucose, and no gas formation from sugar (glucose), is referred to as belonging to genus Pediococcus and genus Streptococcus.

Comparison of these strains with the identification manual of the above references is as follows:

| | Strain B-0667 | Strain B-0668 | genus Pediococcus | genus Streptococcus |
|---|---|---|---|---|
| Growth at 45° C. | − | − | + | d |
| Tolerance at 60° C. for 30 min. | − | + | − | d |
| Glycerol (acid formation) | − | − | − | d |
| Arabinose (acid formation) | − | − | + | d |
| Halotolerance (NaCl 10%) | + | − | + | − |

In table:
+ = positive more than 85%;
− = negative more than 85%;
d = varies among strains or species.

Hence the strain B-0667 will be referred to as genus Pediococcus or Streptococcus. Consulting the above "Manual for the Identification of Medical Bacteria" and J. Gen. Microbiol., 26, 185–197 (1961), the taxonomic properties of the strain B-0667 were almost identical with those of *Pediococcus urina-equi*, however the characteristics described in "Bergey's Manual of Determinative Bacteriology", 8th Ed., 1974 were slightly different therefrom. Therefore the strain B-0667 is referred to as genus Pediococcus and designated as Pediococcus sp. B-0667.

The strain B-0668 resembles genus Streptococcus rather than genus Pediococcus. Further consulting the "Manual for the Identification of Medical Bacteria", the strain B-0668 resembles *Streptococcus faecium* var. *durans*, however no taxonomic properties were described in "Bergey's Manual" and therefore it is impossible to make a detailed comparison. The strain B-0668, therefore, is referred to as Streptococcus sp. B-0668.

The strains B-0667 and B-0668 were deposited for permanent collection in the Institute of Microbial Industry and Technology, Agency of Industrial Science and Technology, M.I.T.I., Japan, as deposition numbers FERM-P No. 4438 and FERM-P No. 4439, respectively. IFO-12219 and IFO-12317 were deposited for permanent collection in the Institute for Fermentation, Osaka, Japan, under those numbers.

In an embodiment of the present invention, the above Pediococcus sp. B-0667, Streptococcus sp. B-0668, *Aerococcus viridans* IFO-12219 or *Aerococcus viridans* IFO-12317 are cultured in a conventional medium for enzyme production. Cultivation can be by conventional liquid culture and submerged aeration culture is preferable for industrial production.

A conventional medium for culturing microorganisms can preferably be used. For the carbon sources, assimilable carbon sources such as glucose, sucrose, lactose, maltose, fructose, molasses, pyruvic acid or the like can preferably be used. Assimilable nitrogen sources such as peptone, meat extract, yeast extract, casein hydrolyzate or the like can be used. Various inorganic salts such as phosphates, carbonates, sulfates, salts of magnesium, calcium, potassium, divalent iron, manganese or zinc can be used.

The culturing temperature can be selected within the range for growth of microbial cells and production of pyruvate oxidase, and is preferably 25°–37° C. The culturing time can be altered depending on conditions and is terminated when the pyruvate oxidase production is substantially complete, and is usually 18–48 hours.

To separate pyruvate oxidase from the culture, the cultured mass is filtered or centrifuged to collect the cells, which are disrupted by treatment with mechanical means or enzymes such as lysozyme. Further if necessary pyruvate oxidase is solubilized by adding ethylenediaminetetraacetic acid (EDTA) and a surfactant such as Triton X-100 (trademark) or Adecatol SO-120 (trademark) to separate the enzyme. The thus-obtained solution of pyruvate oxidase is treated with or without concentration, and thereafter the enzyme is precipitated by salting out with the addition of a soluble salt such as ammonium sulfate or sodium chloride. Low molecular weight impurities are removed by dialysis. Furthermore impurities in the solution of pyruvate oxidase are preferably removed by adsorption chromatography, ion-exchange chromatography or gel filtration. The enzyme solution thus obtained is treated by vacuum concentration and lyophilization to produce powdered pyruvate oxidase. Further purification can be achieved by conventional purification methods for proteins and enzymes such as adsorption chromatography, ion-exchange chromatography or gel filtration.

Pyruvate oxidase produced by the present invention has the following physico-chemical properties, in which abbreviations are used as follows:

| | |
|---|---|
| Pediococcus sp. B-0667: | abbreviated as B-0667; |
| Streptococcus sp. B-0668: | abbreviated as B-0668; |
| Aerococcus viridans IFO-12219: | abbreviated as IFO-12219; |
| Aerococcus viridans IFO-12317: | abbreviated as IFO:12317. |

(1) Enzyme action:

The enzyme catalyzes the oxidative reaction of pyruvic acid, inorganic phosphate and oxygen to form acetylphosphate, carbon dioxide and hydrogen peroxide:

$$CH_3COCOOH + HOPO_3^{--} + O_2 \rightarrow CH_3COOPO_3^{--} + CO_2 + H_2O_2$$

(2) Optimum pH:

Effect of pH on pyruvate oxidase activity is measured. Phosphate buffer solutions of pH 6–8 are used for assay. The results are shown in FIG. 1 in which optimum pH is as follows:

| | |
|---|---|
| B-0667: | pH 6.3–7.5 |
| B-0668: | pH 7.5–8.5 |
| IFO-12219: | pH 7.0–8.0 |
| IFO-12317: | pH 6.8–7.5 |

Slight variation is observed according to phosphate concentration and kind of metallic ion.

Figure 2:
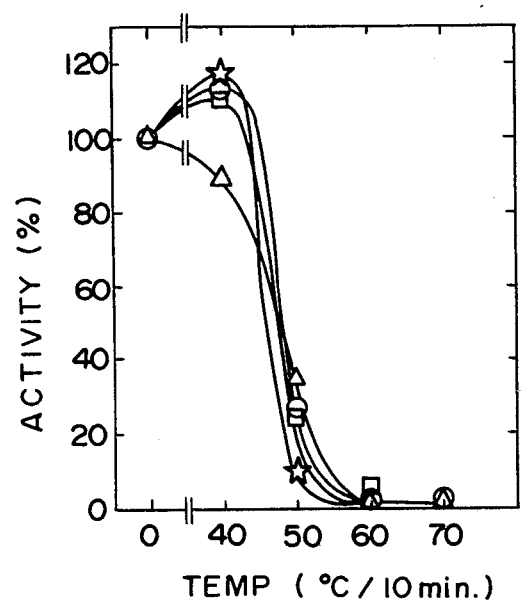
FIG. 2 shows the heat stability of pyruvate oxidase.

(3) Heat stability:

Heat stability of the enzyme is determined by incubating in 10 mM phosphate buffer (pH 6.5) containing 10 $\mu$M FAD at 0°, 40°, 50°, 60° and 70° C. for 10 minutes according to the method of enzyme assay. As shown in FIG. 2 the enzymes obtained from B-0667, IFO-12219 and IFO-12317 are slightly activated at 40° C. and denatured above 60° C. The enzyme obtained from B-0668 is not activated at 40° C. and almost denatured above 60° C.

Figure 3:
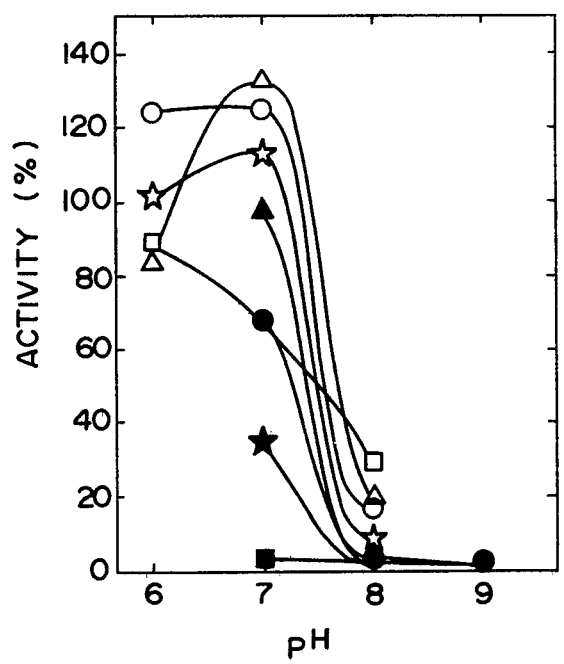
FIG. 3 shows the pH stability of pyruvate oxidase.

(4) pH stability:

To each enzyme solution (0.1 ml) is added 0.2 M phosphate buffer for pH 6–8 (0.9 ml) or 0.2 M of Tris-HCl buffer for pH 7–9 (0.9 ml) each containing 10 $\mu$M FAD, and allowed to stand for 10 minutes at 40° C. 20 $\mu$l of enzyme solution are taken and enzyme activity is determined. As shown in FIG. 3, the enzyme obtained from B-0667, IFO-12219 and IFO-12317 is most stable at about pH 7 and that of B-0668 is stable at an acidic pH.

(5) Effect of several substances:

(a) Effect of several substances on the enzyme activity is examined by adding 5 mM of the substance indicated below instead of $MgCl_2$ in the assay system.

| | Relative activity (%) | | | |
|---|---|---|---|---|
| Substance added | B-0667 | B-0668 | IFO-12219 | IFO-12317 |
| No addition | 25.4 | 72.0 | 42.0 | 50.3 |
| EDTA | 0 | 0 | 0 | 0 |
| $MgCl_2$ | 100 | 100 | 100 | 100 |
| $CaCl_2$ | 69.4 | 75.0 | 83.4 | 78.7 |
| $MnCl_2$ | 129.1 | 102.7 | 116.2 | 111.0 |
| $CoCl_2$ | 81.3 | 81.1 | 85.0 | 84.0 |
| $BaCl_2$ | 20.6 | 58.8 | 23.9 | 28.8 |
| $ZnCl_2$ | 16.0 | 38.2 | 14.9 | 22.8 |

As shown hereinabove, the enzyme is inhibited by EDTA and activated by $Mg^{++}$, $Ca^{++}$, $Mn^{++}$ and $Co^{++}$.

(b) Effect of elimination of the following substance from the assay system on the enzyme activity is shown below. 0.1 M dimethylglutarate-NaOH buffer is used in the case of phosphate elimination.

| | Relative activity (%) | | | |
|---|---|---|---|---|
| Substance eliminated | B-0667 | B-0668 | IFO-12219 | IFO-12317 |
| No elimination | 100 | 100 | 100 | 100 |
| Thiaminepyrophosphate | 0 | 0 | 0 | 0 |
| FAD | 33.9 | 100 | 32.7 | 41.7 |
| Thiaminepyrophosphate and FAD | 0 | 0 | 0 | 0 |
| Phosphate | 0 | 0 | 0 | 0 |

As a result, the enzyme requires thiaminepyrophosphate and FAD as cofactor and phosphate as substrate.

Further, oxygen consumption during enzyme reaction is measured by oxygen-electrode, and the oxygen is consumed in proportion to an enzyme activity (formation of hydrogen peroxide). Results are shown in the following:

| | Oxygen Consumption ($\mu$ mole/min.) | Reaction product ($\mu$ mole/min.) | |
|---|---|---|---|
| | | $H_2O_2$ | Acetylphosphate |
| B-0667 | 0.042 | 0.042 | 0.038 |
| B-0668 | 0.022 | 0.0213 | 0.020 |
| IFO-12219 | 0.040 | 0.038 | 0.037 |
| IFO-12317 | 0.035 | 0.036 | 0.034 |

Assays are performed as follows:

Oxygen consumption: dissolved oxygen meter (tradename; YSI-dissolved oxygen meter Model-53).

Acetylphosphate: F. Lipman et al., J. Biol. Chem., 134, 463–464 (1940).

Hydrogen peroxide: method using N,N-dimethylaniline, 4-aminoantipyrin and horseradish peroxidase.

As hereinabove explained, the enzyme obtained from the above four strains is referred to as pyruvate oxidase and flavine protein.

The assay method of pyruvate oxidase of the present invention uses a reaction mixture as follows:

| | |
|---|---|
| 0.5 M potassium pyruvate | 0.1 ml |
| 0.5 M phosphate buffer (pH 7.9) | 0.2 ml |
| 0.2% 4-aminoantipyrin | 0.1 ml |
| 0.2% N,N-dimethylaniline | 0.2 ml |
| 0.2 M MgCl$_2$ | 50 μl |
| 10 mM thiaminepyrophosphate | 20 μl |
| peroxidase (45 U/ml) | 0.1 ml |
| 1 mM FAD | 10 μl |
| distilled water | 0.22 ml |

The above reaction mixture (1.0 ml) is pre-incubated at 37° C. for 3 minutes. To this solution is added the enzyme solution (20 μl) and incubated at 37° C. for 10 minutes. 0.1 M citrate buffer (pH 6.0, 2 ml) containing 0.1 M EDTA is added to stop the reaction. The violet color formed is measured by colorimetric method at 565 nm.

A unit (1 unit, 1 U) of enzyme activity is defined as the activity which generates 1 μmole of hydrogen peroxide per minute.

In order to activate the pyruvate oxidase reaction system, FAD, thiaminepyrophosphate and phosphate are added. Further for activation of the enzyme, an ion-liberating salt which liberates calcium ions, cobalt ions, magnesium ions or manganese ions, in the form of chloride is preferably added thereto. An indicator such as a coloring indicator or fluorescent indicator for hydrogen peroxide can preferably be used.

The amount and ratio of components in the enzyme reaction system can be selected for substantial enzyme reaction and will be varied according to the amount of pyruvate, temperature and time of enzyme reaction. For example, 1–20 U of pyruvate oxidase, 0.1–20 μmoles of FAD, 0.05–0.5 μmole of thiaminepyrophosphate, 1–10 μmoles of inorganic phosphate and 0.05–10 μmoles of ion liberating salt per test can preferably be used. Pyruvate oxidase can be in a microcapsulated form or in an immobilized form of covalent linkage with an organic or inorganic carrier or adsorbed on a carrier. The molar ratio of indicator for hydrogen peroxide is at least an equimolar or excess amount of generated hydrogen peroxide. In the case of the peroxidase, 0.5–20 U per test is preferably used. These components of the enzymatic reaction mixture are preferably used by dissolving in the buffer of suitably adjusted pH.

The thus-prepared enzymatic reaction system is used for the analysis of pyruvic acid. Any samples which contain pyruvate can be analyzed. For example, pyruvic acid itself, pyruvic acid in serum or urine and pyruvic acid-forming enzyme reaction systems such as lactic acid and lactate dehydrogenas (LDH), ADP and pyruvate kinase, and glycerol, glycerol kinase and pyruvate kinase can be mentioned. Further detailed examples of the enzymatic reactions which form pyruvic acid and so can be assayed are as follows:

(1) Assay of lactic acid or LDH activity:

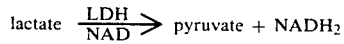

(2) Assay of ADP or pyruvate kinase (PK) activity:

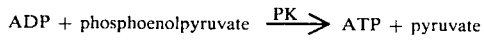

(3) Assay of glutamate-pyruvate-transaminase (GPT) activity or α-ketoglutarate:

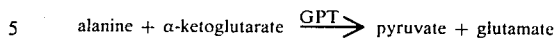

(4) Assay of glutamate-oxaloacetate-transaminase (GOT) activity:

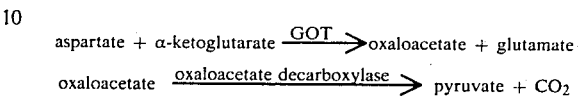

(5) Assay of glycerol or glycerophospho kinase (GK) activity:

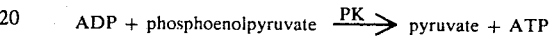

(6) Assay of triglyceride:

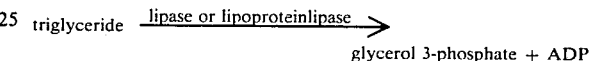
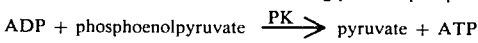

(7) Assay of creatinine or creatinine phosphokinase (CPK):

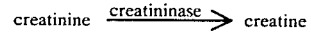
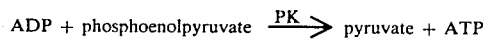

(8) Assay of myokinase:

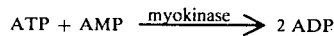

(9) Assay of fatty acid or thiokinase activity:

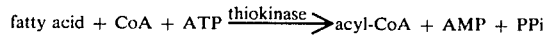
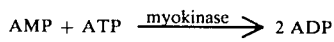

These enzyme reactions are only for illustration and these pyruvate-forming reactions can be performed with the combination of enzyme and its substrate, for example a biological sample. As exemplified hereinabove, the assay can be applied not only for assay of pyruvate but also for assay of enzyme, enzyme activity or substrate.

Assay is performed by incubation with the sample and a reagent mixture. The reagent mixture is preferably a kit of necessary reagents. For assaying, consumed component or generated component is measured. Measuring the amount of oxygen consumption by dissolved oxygen meter is preferable as an assay method. In this case no indicator for hydrogen peroxide is necessary. As for the assaying of a generated component, measurement of the amount of hydrogen peroxide is preferable, for example by a hydrogen peroxide electrode meter such as a YSI-oxidase meter or by colorimetric or fluorometric assay with an indicator for hydrogen peroxide. The assay can be performed preferably for 10–60 minutes and at 20°–40° C., preferably at 35°–37° C.

The indicator for hydrogen peroxide is a combination of one or more chromogen or fluorescents, which is effected by coupling with hydrogen peroxide. Examples of such indicators are combinations of tetravalent titanium compounds and xylenol orange which couples with hydrogen peroxide to form a stable red color, or a combination of phenol or N,N-dimethylaniline or homovanillic acid, 4-aminoantipyrin and peroxidase for measuring color or fluorescence. 4-aminoantipyrin can be replaced by 4-aminophenazone. A combination of 2,6-dichlorophenol indophenol and peroxidase and of guaiacol and peroxidase can also be used. The indicator can be previously prepared as a solution. Colorimetric or fluorometric assay is performed by measuring the absorption at a suitable wave length such as 565 nm.

The amount of pyruvic acid can be measured by calculation from corresponding standard curves of consumed oxygen or generated hydrogen peroxide.

Phosphate as a consumed component or acetylphosphate as a generated component can also be assayed by any conventional method.

As hereinabove explained, a kit for analysis, especially quantitative analysis, comprises pyruvate oxidase. More particularly, as illustrated hereinbefore, diagnostic analysis such as analysis of pyruvate in pyruvate-containing reagents or in serum or urine, assay of enzyme activity of LDH, pyruvate kinase, GPT, GOT, glycerol kinase, lipase, lipoprotein lipase, creatinine phosphokinase, myokinase or thiokinase, and analysis of biological components such as lactate, ADP, glycerol, triglyceride, creatinine or fatty acids can advantageously be carried out with the kit and by the method of the present invention.

The following examples illustrate the embodiments of the present invention but are not to be construed as limiting the invention.

EXAMPLE 1

Four samples of culture medium (each 100 ml, pH 7) comprising glucose (1%), peptone (1%), yeast extract (0.5%), NaCl (0.2%), $KH_2PO_4$ (0.1%), $K_2HPO_4$ (0.1%), $MgSO_4$ (0.05%) and $CaCO_3$ (0.3%) in a 500 ml Erlenmyer flask were sterilized at 120° C. for 20 minutes. To each medium was inoculated a strain of Pediococcus sp. B-0667 FERM-P No. 4438, Streptococcus sp. B-0668 FERM-P No. 4439, Aerococcus viridans IFO-12219 or Aerococcus viridans IFO-12317, respectively and shake-cultured at 30° C. for 24 hours, at 300 r.p.m. Thereafter cultured cells centrifugally collected were washed with 10 mM phosphate buffer (pH 6.5) and again centrifuged to collect bacterial cells. The thus-obtained cells were suspended in 10 mM phosphate buffer (10 ml, pH 7.0) containing 0.02% lysozyme and 0.1% Triton X-100 and incubated at 37° C. for 60 minutes. The supernatant obtained centrifugally which contains pyruvate oxidase was collected. Enzyme activity of the supernatant is shown in the following table.

| Strain | Enzyme activity (U/ml) |
| --- | --- |
| B-0667 | 0.60 |
| B-0668 | 0.38 |
| IFO-12219 | 0.52 |
| IFO-12317 | 0.46 |

EXAMPLE 2

A medium (20 l.) consisting of the same components as described in Example 1 in a 30 l. jar-fermenter was sterilized by steam. Cultured broth (200 ml) of Pediococcus sp. B-0667 FERM-P No. 4438 cultured the same way as in Example 1 was transferred thereto, and cultured at 30° C. for 24 hours. Bacterial cells centrifugally collected (about 100 g) were suspended in lysozyme solution (0.2 mg/ml, 4 l.), and there was further added Triton X-100 (trademark, 4 g), EDTA (3 g) and 1 M phosphate buffer (pH 6.5, 40 ml) and the mixture was stirred at 37° C. for 60 minutes. To the supernatant obtained centrifugally was added ammonium sulfate and the precipitate at 0.54–0.73 saturation was collected by centrifugation. The precipitate was dissolved in 10 mM phosphate buffer (pH 6.5, 1000 ml) (5160 U, recovery: 86%), then cold acetone (0.65 volume) was added thereto and the impure precipitate was separated. Acetone (0.3 volume) was then added and the precipitate, which was collected by centrifugation, was dissolved in 10 mM phosphate buffer (pH 6.5, 70 ml) (4750 U, recovery: 79.2%).

To the solution was added ammonium sulfate and the precipitate at 0.54–0.70 saturation was collected centrifugally.

After dissolving the precipitate in 10 mM phosphate buffer (pH 6.5), the solution was charged on a column of Sephadex G-25 (trademark) (6.0×70 cm) and the fraction was collected showing absorbency at 280 nm. The active fractions were pooled and freeze dried to obtain powdered pyruvate oxidase (3940 U, 758 mg. recovery: 65.7%).

EXAMPLE 3

A composition for pyruvate analysis by oxygen electrode comprises the following:

| | | |
| --- | --- | --- |
| pyruvate oxidase obtained in Example 2 (the same as in the following examples) | 300 | U |
| FAD | 0.5 | μ mole |
| thiamine pyrophosphate | 10 | μ moles |
| $MnCl_2$ | 25 | μ moles |
| 0.2 M phosphate buffer (pH 7.5) | 1.0 | ml |
| sucrose | 0.5 | g |
| 0.2 M dimethylglutarate-NaOH buffer (pH 7.5) | 5 | ml |

The above mixture is lyophilized for use in a kit for assay of pyruvic acid (by oxygen electrode measurement, 50 tests).

EXAMPLE 4

A kit composition for pyruvate analysis by colorimetric assay comprises the following:

| | | |
| --- | --- | --- |
| Reagent (I) | | |
| pyruvate oxidase | 200 | U |
| FAD | 0.5 | μ mole |
| thiamine pyrophosphate | 10 | μ moles |
| 0.2 M phosphate buffer (pH 7.5) | 1.0 | ml |
| sucrose | 0.5 | g |
| 0.2 M dimethylglutarate-NaOH buffer | | |

| | | |
|---|---|---|
| (pH 7.5) | 5 | ml |
| peroxidase (100 U/mg, horseradish) | 2.5 | mg |
| 0.3% 4-aminoantipyrin | 5 | ml |

The above mixture is lyophilized to prepare the reagent (I) of the kit for pyruvate analysis (by colorimetry, 50 tests).

Additional reagent (II) consisting of 0.2% aqueous N,N-dimethylaniline containing 25 μmoles $MnCl_2$ (50 ml) and stop reagent (III) consisting of 0.1 M citrate buffer (pH 6.05, 100 ml) containing 0.1 M EDTA were the other ingredients of the kit.

EXAMPLE 5

The composition of Example 3 was dissolved in distilled water (50 ml) and an aliquot solution (1.0 ml) thereof was put in reaction vessels. Thereto was added 5.0 mM pyruvate solution (each 0–100 μl), or human serum 50 μl and 5.0 mM pyruvate solution (each additionally 0–100 μl), and the mixture was incubated at 37° C., then the oxygen consumption was measured by Galvanic oxygen electrode. Results are shown in FIG. 4.

Further, the composition of Example 3 was dissolved in distilled water (25 ml) and an aliquot solution (0.5 ml) thereof was put in reaction vessels and then incubated with the addition of an aqueous solution (0.5 ml) containing human serum (0–0.5 ml) at 37° C. In FIG. 5 is shown the result of assay of oxygen consumption measured by Galvanic oxygen electrode.

As shown in FIGS. 4 and 5, good linear relations were observed.

EXAMPLE 6

Figure 6:
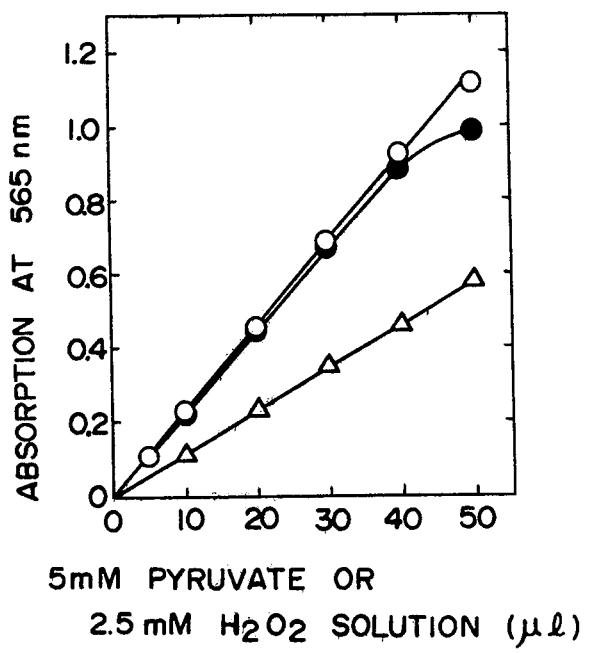
FIG. 6 shows the results of analysis of pyruvic acid by colorimetric method using pyruvate oxidase.

The lyophilized reagent (I) prepared in Example 4 was dissolved by addition of reagent (II) (50 ml), and plural aliquot solutions (1 ml) in small test tubes were incubated at 37° C. Thereto was added 5 mM potassium pyruvate solution (each 0–50 μl), or human serum (50 μl) along with 5 mM potassium pyruvate solution (each 0–50 μl), and the mixtures were incubated at 37° C. for 10 minutes. Stop solution (2 ml) was added to each and the absorbency at 565 nm was measured. As shown in FIG. 6, good linear relations and quantitative results were observed in the above assays and this results also coincided with the calibration curve by $H_2O_2$ (2.5 mM $H_2O_2$, 0–50 μl).

Further aliquot samples of human serum (0–0.5 ml) were put into small test tubes and adjusted to 0.5 ml by adding distilled water. Each solution (1.0 ml) of reagent (I) prepared with added reagent (II) in Example 4 was added thereto, and the mixtures were incubated at 37° C. for 10 minutes. Reaction was stopped by adding stop reagent (III) (1.5 ml) and the mixtures were colorimetrically assayed at 565 nm. As shown in FIG. 7, good quantitative results were obtained.

EXAMPLE 7

| Reaction mixture: | | |
|---|---|---|
| 0.2 M dimethylglutarate-NaOH buffer (pH 7.5) | 0.2 | ml |
| 10 mM $MnCl_2$ | 50 | μl |
| 0.2% N,N-dimethylaniline | 0.2 | ml |
| 0.3% 4-aminoantipyrin | 0.1 | ml |
| peroxidase (45 U/ml) | 0.1 | ml |
| 10 mM thiamine pyrophosphate | 20 | μl |
| 0.2 M phosphate buffer (pH 7.5) | 25 | μl |
| 20 mM phosphoenolpyruvate | 0.1 | ml |
| pyruvate kinase (4000 U/ml) | 5 | μl |
| 5 mM ADP | 0–50 | μ |

Figure 8:
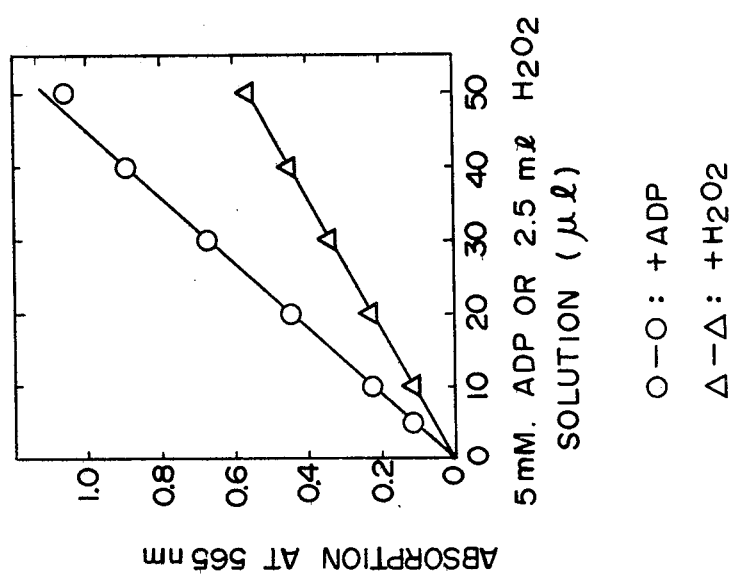
FIG. 8 shows the results of analysis of ADP using pyruvate oxidase.

The above reaction mixture was adjusted to 1.0 ml by adding distilled water, pre-incubated at 37° C., then a solution of pyruvate oxidase (200 U/ml, 20 μl) was added thereto, and the mixture was incubated at 37° C. for 10 minutes. After stopping the reaction with the addition of 0.1 M EDTA in 0.1 M citrate buffer (pH 6.0, 2.0 ml), the absorbency at 565 nm was measured. As shown in FIG. 8, good quantitative results of ADP assay were observed by assaying hydrogen peroxide generated from the reaction mixture of ADP, pyruvate kinase, phosphoenolpyruvate and others.

Also as shown in FIG. 8, good linearity was observed when 2.5 mM hydrogen peroxide was used instead of 5 mM ADP.

EXAMPLE 8

| Triglyceride assay kit: | | |
|---|---|---|
| Reagent (I) | | |
| 0.2 M dimethylgultarate-NaOH buffer (pH 7.5) | 10 | ml |
| 0.3% 4-aminoantipyrin | 5 | ml |
| peroxidase (100 U/mg) | 2.5 | mg |
| thiamine pyrophosphate | 10 | μ moles |
| 0.2 M phosphate buffer (pH 7.5) | 1.25 | ml |
| phosphoenolpyruvate | 100 | μ moles |
| pyruvate kinase (4000 U/ml) | 0.1 | ml |
| pyruvate oxidase (200 U/ml) | 2 | ml |
| lipoprotein lipase (3000 U/ml) | 0.5 | ml |
| glycerol phosphokinase (300 U/ml) | 1.0 | ml |
| ATP | 100 | μ moles |
| The above reagent was lyophilized. | | |
| Reagent (II) | | |
| 25 μ moles of $MnCl_2$ in 0.2% dimethylaniline | 50 | ml |
| Reagent (III) (stopper solution) | | |
| 0.1 M EDTA in 0.1 citrate buffer (pH 6.0) | 100 | ml |

EXAMPLE 9

Reagent (I) in Example 8 was dissolved in reagent (II) and each aliquot solution (1.0 ml) thereof was put in test tubes.

Figure 9:
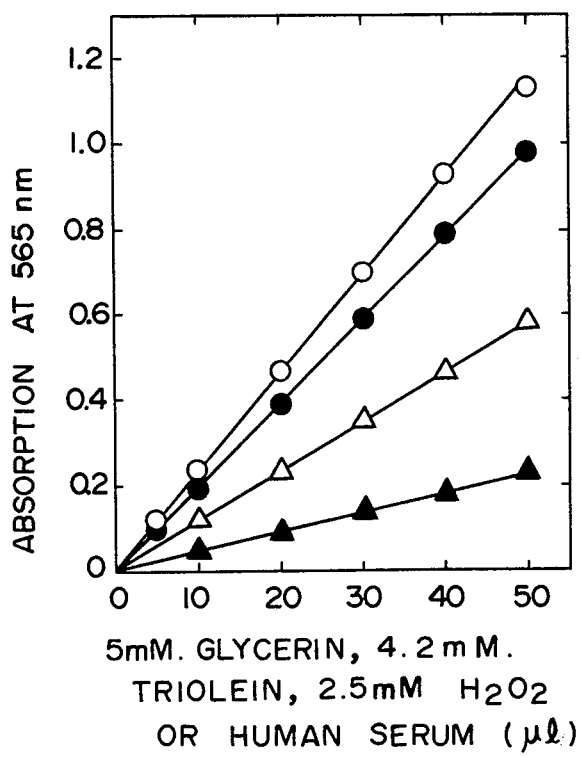
FIG. 9 shows the results of analysis of glycerol, triglyceride and serum triglyceride using pyruvate oxidase.

Each aliquot sample (0–50 μl) of human serum containing 1.02 μmole/ml of triglyceride, 5 mM glycerol solution, 4.2 mM triolein in 0.1% Triton X-100 solution or 2.5 mM hydrogen peroxide solution, respectively, was added thereto and the mixtures were incubated at 37° C. for 10 minutes. As shown in FIG. 9, good linearities were observed.

EXAMPLE 10

| A kit for assay of serum transaminase (for 100 tests): | | |
|---|---|---|
| (1) A kit for GTP assay (for 100 tests): | | |
| Reagent (I): lyophilized reagent consisting of the following: | | |
| pyruvate oxidase | 400 | U |
| FAD | 500 | n moles |
| thiamine pyrophosphate | 150 | μ moles |
| L-alanine | 20 | m moles |
| α-ketoglutarate | 1 | m mole |
| sucrose | 1 | g |
| 4-aminoantipyrin | 150 | μ moles |
| peroxidase | 450 | U |
| 0.2 M phosphate buffer (pH 7.5) | 2.5 | ml |

-continued

| | | |
|---|---|---|
| 0.2 M dimethylglutarate-NaOH buffer (pH 7.5) | 30 | ml |
| Reagent (II) (100 ml are used for Reagent (I)): | | |
| 42 μ moles MnCl$_2$ in 0.2% dimethylaniline solution | 210 | ml |
| Reagent (III) (stopper solution; 200 ml for Reagent (I), 2.0 ml per one test): | | |
| 0.1 M EDTA in 0.2 M citrate buffer (pH 5.0) | 420 | ml |
| (2) A kit for GOT assay (for 100 tests): | | |
| Reagent (I): lyophilized reagent consisting of the following: | | |
| pyruvate oxidase | 400 | U |
| FAD | 500 | n moles |
| thiamine pyrophosphate | 150 | μ moles |
| L-aspartic acid | 20 | m moles |
| α-ketoglutarate | 1 | m mole |
| oxaloacetate decarboxylase | 200 | U |
| sucrose | 1 | g |
| 4-aminoantipyrin | 150 | μ moles |
| peroxidase | 450 | U |
| 0.2 M phosphate buffer (pH 7.5) | 2.5 | ml |
| 0.2 M dimethylglutarate-NaOH buffer (pH 7.5) | 30 | ml |
| Reagent (II) and Reagent (III): The same as (1) above. | | |

EXAMPLE 11

Figure 10:
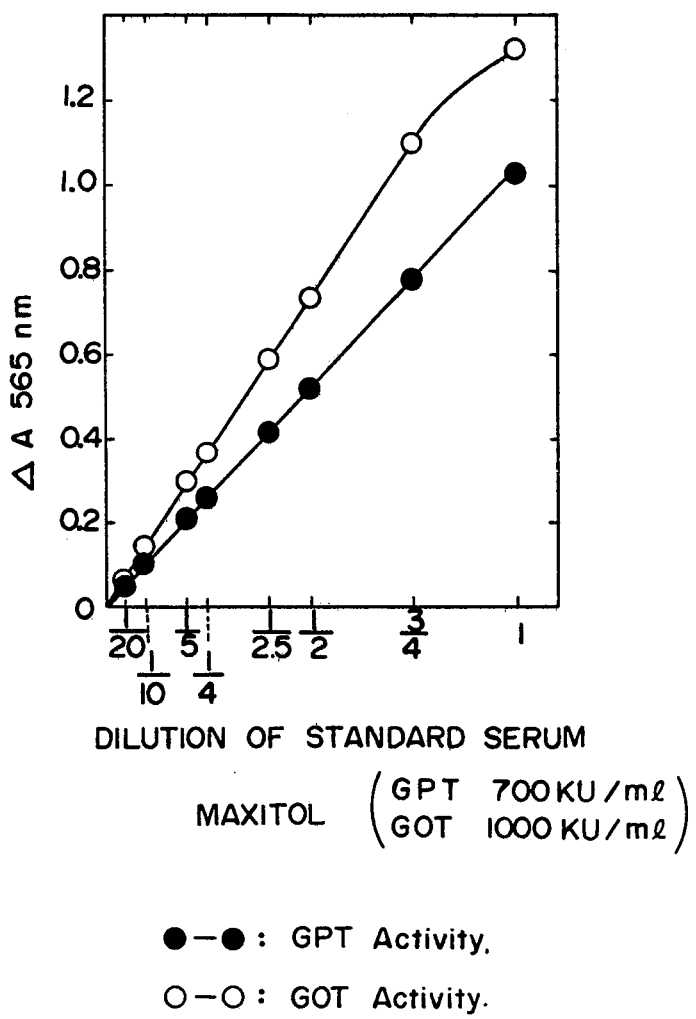
FIG. 10 shows the results of analysis of GPT- and GOT-activity using pyruvate oxidase.

Reagents (I) prepared in Example 10, (1) (for GPT activity assay) and (2) (for GOT activity assay), were dissolved by adding reagent (II) (100 ml) to each. Each aliquot amount (1.0 ml) of the solution was separately put into small test tubes and pre-incubated at 37° C. for 5 minutes (pre-incubated solution of reagent (I)). The standard serum solution (20 μl) (Calbiochem Co., trademark Maxitol, containing GPT 700 K U/ml and GOT 1000 K U/ml diluted with constant ratio was added thereto and incubated at 37° C. for 10 minutes. Reaction was stopped by adding stopping reagent (III) (2.0 ml) and the absorbency at 565 nm was measured. As shown in FIG. 10, both enzyme activities have linearity up to the optical density of about 1.0 (enzyme activity: about 750 K U/ml).

EXAMPLE 12

To each pre-incubated solution of reagent (I) obtained in Example 11 were added 20 μl of human serums (45 samples) and the mixtures were incubated at 37° C. for 20 minutes. Stopping reagent (III) (2.0 ml) was added therein and the absorbency at 565 nm was measured.

Also the same samples of human sera were assayed by LKB method (ultra violet absorption method, GOT assay kit and GPT assay kit, made by LKB Corp.) and the correlation was plotted with activity of GPT and GOT.

As shown in FIG. 11, the correlation coefficient: $r = 0.998$ and regression equation: $y = 0.00295 \times + 0.0032$ for GPT assay were observed.

Figure 12:
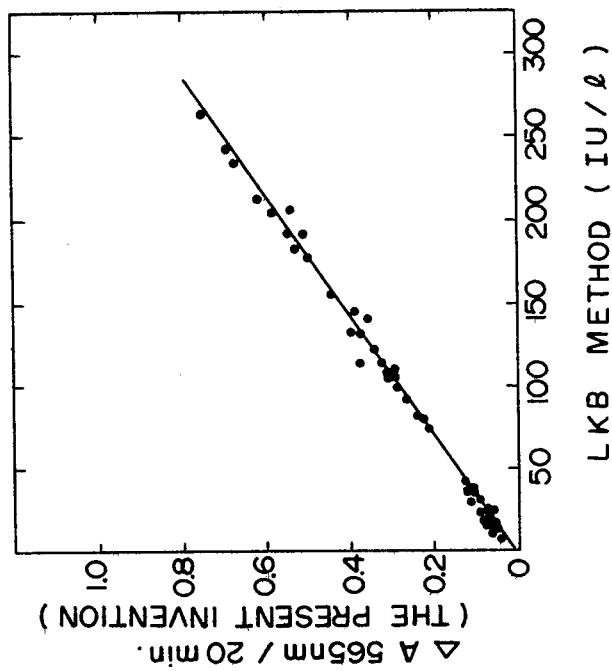
FIG. 12 is a correlation diagram of analysis of GOT-activity using pyruvate oxidase.

For GOT assay, the correlation pattern is shown in FIG. 12, in which the correlation coefficient: $r = 0.966$ and regression equation: $y = 0.00287 \times + 0.0180$ resulted.

From a consideration of the foregoing disclosure, therefore, it will be evident that the initially recited objects of the present invention have been achieved.

Although the present invention has been described and illustrated in connection with preferred embodiments, it is to be understood that modifications and variations may be restored to without departing from the spirit of the invention, as those skilled in this art will readily understand. Such modifications and variations are considered to be within the purview and scope of the present invention as defined by the appended claims.

What is claimed is:

1. A process for the manufacture of pyruvate oxidase, which comprises culturing a pyruvate oxidase-producing microorganism belonging to a genus selected from Pediococcus, Streptococcus and Aerococcus, in a nutrient culture medium, and separating the pyruvate oxidase thus produced from the culture medium.

2. A process as claimed in claim 1, in which said microorganism is selected from the group consisting of Pediococcus sp. B-0667, Streptococcus sp. B-0668, Aerococcus viridans IFO-12219 and Aerococcus viridans IFO-12317.

3. A method for the analysis of pyruvic acid in a sample containing pyruvic acid or a pyruvate-liberating system, comprising contacting said sample with pyruvate oxidase and measuring a consumed component or a generated component, in which said reaction system contains at least pyruvate oxidase, FAD, thiamine pyrophosphate, phosphate and a salt which liberates ions selected from the group consisting of calcium cobalt, magnesium and manganese.

4. A method as claimed in claim 3, in which said system also contains an indicator for hydrogen peroxide.

5. A method as claimed in claim 4, in which said indicator for hydrogen peroxide is selected from the group consisting of peroxidase, 4-aminoanitipyrin, phenol, N,N-dimethylaniline and homovanillic acid.

6. A method as claimed in claim 3, in which a consumed component is measured and said consumed component is oxygen.

7. A method as claimed in claim 3, in which a generated component is measured and said generated component is hydrogen peroxide.

8. A kit for the analysis of pyruvic acid, comprising a plurality of separate compositions one of which contains at least pyruvate oxidase, FAD, thiamine pyrophosphate and phosphate and another of which contains at least a salt which liberates an ion selected from the group consisting of calcium, cobalt, magnesium and manganese.

9. A kit as claimed in claim 8, containing also an indicator for hydrogen peroxide.

10. A kit as claimed in claim 9, in which said indicator for hydrogen peroxide is a member selected from the group consisting of peroxidase, 4-aminoanitipyrin, phenol, N,N-dimethylaniline and homovanillic acid.

* * * * *